United States Patent [19]
Johnson et al.

[11] Patent Number: 5,740,810
[45] Date of Patent: Apr. 21, 1998

[54] ONE HAND PUSH BUTTON FAST FLUSH DEVICE

[75] Inventors: Robert H. Johnson, Fountain Green; Gordon S. Reynolds, Bountiful, both of Utah

[73] Assignee: Abbott Laboratories, Abbott Park, Ill.

[21] Appl. No.: 480,224

[22] Filed: Jun. 7, 1995

Related U.S. Application Data

[63] Continuation-in-part of Ser. No. 173,549, Dec. 23, 1993, abandoned.

[51] Int. Cl.$^6$ ............................................. A61B 5/00
[52] U.S. Cl. ...................... 128/673; 128/675; 251/117; 137/902
[58] Field of Search ........................... 251/117, 320, 251/321, 903; 137/902; 128/673, 5, 748; 604/30, 32–34, 246–256

[56] References Cited

U.S. PATENT DOCUMENTS

| | | |
|---|---|---|
| 3,675,891 | 7/1972 | Reynolds . |
| 4,341,224 | 7/1982 | Stevens ................................. 251/117 |
| 4,550,748 | 11/1985 | Nunez .................................. 251/117 |
| 4,696,305 | 9/1987 | von Berg ............................. 128/673 |
| 4,936,542 | 6/1990 | Beard ................................... 251/117 |

Primary Examiner—Robert L. Nasser
Attorney, Agent, or Firm—Neal D. Marcus; Ronald M. Anderson

[57] ABSTRACT

A flush device for an intravenous blood pressure monitoring system has a main body which includes a continuous capillary flow channel and a fast flush channel. The continuous capillary flow channel is separated from the fast flush channel by a median wall. A fast flush opening in the median wall is blocked by an elastomeric member. When the member is distended, the fast flush opening is unblocked. An alternative embodiment of the fast flush device has a tubular body with a capillary channel formed on an inner wall. An elastomeric member contained within the tubular body enables flow to the capillary channel when the elastomeric member is in an initial position. When the elastomeric member is in a distended position fluid is allowed to overflow the capillary channel thus permitting a fast flush flow. Another alternative embodiment of the flush device comprises a tubular body having a cylinder disposed within, with a fluid entry chamber defined in an annular space and a fluid exit chamber defined by the interior of the cylinder. A microbore in the cylinder wall enables continuous capillary flow from the inlet to the outlet. A fast flush opening, blocked by an elastomeric member, is also provided in the cylinder wall. When the member is distended, the fast flush opening is unblocked.

13 Claims, 6 Drawing Sheets

ONE HAND PUSH BUTTON FAST FLUSH DEVICE

This application is a continuation-in-part of U.S. application Ser. No. 08/173,549, filed Dec. 23, 1993, now abandoned.

BACKGROUND OF THE INVENTION

The present invention relates to a continuous fluid flow device; more particularly the present invention relates to a continuous fluid flow device which incorporates a fast flush capability.

In invasive blood pressure monitoring systems a catheter is placed within the vein or artery of a patient in order to sense the pressure of flowing blood. The sensed blood pressure is transmitted through the catheter to a pressure transducer which converts the sensed blood pressure into a pattern of electrical signals which in turn can be displayed on a visual monitor or recorded on a printed chart. If the end of the pressure sensing catheter becomes occluded or masked by the formation of a blood clot or thrombus, the blood pressure monitoring system will produce erroneous signals. Consequently, it is necessary to maintain a small continuous flow of medical liquid through the catheter to reduce the likelihood of formation of blood clots at the end of the catheter.

Additionally, it is desirable to purge air from the catheter on initial filling. This may easily be accomplished by providing a flush device which will allow a substantially larger bolus of fluid to fast flush the catheter. There is also a need to clear the catheter of blood or mixed blood and fluid after blood sampling procedures.

Representative of typical flush devices are those illustrated in U.S. Pat. No. 3,675,891 and U.S. Pat. No. 4,464,179. These two patents illustrate flush devices which utilize two separate channels for liquid flow. Specifically, there is a micro-bore continuous flow channel and a purge or fast flush channel. The continuous flow channel usually consists of a tube having a very small bore or capillary while the purge or fast flush channel is separate and apart from the continuous flow channel and is usually substantially larger in diameter.

Additionally the use of an elastomeric member to provide a blockage for the fast flush channel is shown in U.S. Pat. No. 4,696,305. Similar elastomeric members used in conjunction with a flush device are shown in U.S. Pat. Nos. 4,457,487 and 4,275,675.

In U.S. Pat. No. 4,696,305 a separate glass resistor is disposed in the continuous flow capillary channel. it would be desirable to eliminate additional components of the device such as the glass restrictor and to be able to provide a main body portion which includes a minimum of parts including a capillary bore laser drilled through the main body portion and a separate fast flush channel. It is also desirable to minimize the number of parts in the assembly.

As the continuous flow or capillary channel is extremely small, there is always the chance that clogging of the channel may result in a stoppage of the required continuous low flow of fluid. Such stoppages may be caused by particulate matter or impurities found in the medical liquid. There is, therefore, also a need in the art to provide a device that provides a single channel which may be easily cleared if a stoppage occurs.

It is also necessary to calibrate the dynamic response of the blood pressure monitoring system by sending an impulse or step function of pressure through the catheter and associated pressure tubing to provide a high quality square wave which can be visualized on the display monitor or printed chart. The oscillation and damping of the square wave by the various components in the pressure monitoring system are indicative of the frequency response of the system. Blood pressure measurement techniques are discussed at length in the article entitled "Direct Blood Pressure Measurement-Dynamic Response Requirements" by Reed M. Gardner, Ph.D., *Anesthesiology*, Vol. 54, No. 3, March 1981. Related articles include "Safety and Efficacy of Continuous Flush Systems for Arterial and Pulmonary Artery Catheters" by Reed M. Gardner, Ph.D., Edward L. Bond, Ph.D., and Justin L. Clark, Ph.D., *The Annals of Thoracic Surgery*, Vol. 23, No. 6, June 1977 and "Catheterflush System for Continuous Monitoring of Central Arterial Pulse Waveform, by Reed M. Gardner, Homer R. Warner, Alan F. Toronto and Walter d. Gaisford, Dept. of biophysics and bioengineering, University of Utah, Latter-day Saints Hospital, Salt Lake City, Utah, *Journal of Applied Physiology*, Vol. 29, No. 6, December 1970. To the extent that the above articles will aid in the understanding of the present invention, they are incorporated herein by reference.

An alternative embodiment of the present invention provides a flush device with a single flow path for medical liquid. The single flow path both provides a continuous low flow of medical liquid to continuously purge the end of the catheter and also provides a larger flow path which enables a bolus of fluid to fast flush both the end of the catheter and the continuous flow channel.

SUMMARY OF THE INVENTION

In a main body position having an inlet and an outlet there is provided a micro bore or capillary continuous flow channel and a purge or fast flush channel. The continuous flow capillary channel is integral with the main body portion of the device and closed at one end, with the closed end having a very small bore or capillary drilled therethrough to permit continuous flow from the inlet to the outlet at a very slow rate.

The fast flush channel is separated from the continuous flow channel by a median wall therebetween. The fast flush channel is also substantially larger in size than the continuous flow channel. An opening at an upper end of the median wall enables passage of fluid from the inlet through the fast flush channel to the outlet. An elastomeric member installed in the fast flush channel blocks the opening in the median wall to block the flow of fluid from the inlet through the fast flush channel to the outlet in a first or blocking position of the member.

The elastomeric member has an internal bore which receives a plunger associated with the device. In the initial position of the member, the plunger is displaced from an upper wall of the main body position. When the plunger is depressed the elastomeric member is distended, moving the elastomeric member away from the opening in a median wall between the continuous flow channel and the fast flush medical liquid to continuously purge the end of the catheter and also provides a larger flow path which enables a bolus of fluid to fast flush both the end of the catheter and the continuous flow channel.

SUMMARY OF THE INVENTION

In a main body position having an inlet and an outlet there is provided a micro bore or capillary continuous flow channel and a purge or fast flush channel. The continuous flow capillary channel is integral with the main body portion of the device and closed at one end, with the closed end having a very small bore or capillary drilled therethrough to permit continuous flow from the inlet to the outlet at a very slow rate.

The fast flush channel is separated from the continuous flow channel by a median wall therebetween. The fast flush channel is also substantially larger in size than the continuous flow channel. An opening at an upper end of the median wall enables passage of fluid from the inlet through the fast flush channel to the outlet. An elastomeric member installed in the fast flush channel blocks the opening in the median wall to block the flow of fluid from the inlet through the fast flush channel to the outlet in a first or blocking position of the member.

The elastomeric member has an internal bore which receives a plunger associated with the device. In the initial position of the member, the plunger is displaced from an upper wall of the main body position. When the plunger is depressed the elastomeric member is distended, moving the elastomeric member away from the opening in a median wall between the continuous flow channel and the fast flush channel thereby enabling fluid to flow from the inlet through the fast flush channel to the outlet in a fast flush position. It is particularly advantageous to provide a capillary opening in the main body portion at the end of the continuous flow channel to eliminate such members as a glass restrictor having a continuous micro-bore extending therethrough as shown in the above noted von Berg patent.

In an alternate configuration of the present invention, a flush device has a substantially tubular body. Formed on the inner wall of the tubular body is a capillary or continuous flow channel which runs the length of the tubular body. The capillary channel provides fluid communication between an inlet at one end of the tubular body and an outlet at the other end. Positioned within the tubular body is an elastomeric member which, in its initial position, sealingly engages the inner wall of the tubular body, particularly that portion of the inner wall of the tubular body adjacent the continuous flow channel. Continuous flow fluid from the inlet to the outlet is through the capillary channel formed on the inner wall of the tubular body.

When it is desired to provide a fast flush from a source of medical fluid through the flush device, a plunger contained with the elastomeric member is manually activated. The motion of the plunger causes the elastomeric member to move from an initial position to a distended position. This, in turn causes the elastomeric member to move away from the inner wall of the tubular body. Flow of medical fluid thereby overflows the continuous flow capillary channel as it is no longer restricted to the continuous flow channel by the elastomeric member. When the elastomeric member is returned to its initial position, the overflow position is terminated and flow is once again restricted to a slow flow rate through the continuous flow channel on the inner wall of the tubular body.

BRIEF DESCRIPTION OF THE DRAWINGS

A further understanding of the medical flush device of the present invention may be had by reference to the drawings wherein.

DETAILED DESCRIPTION OF THE EMBODIMENTS

Figure 1:
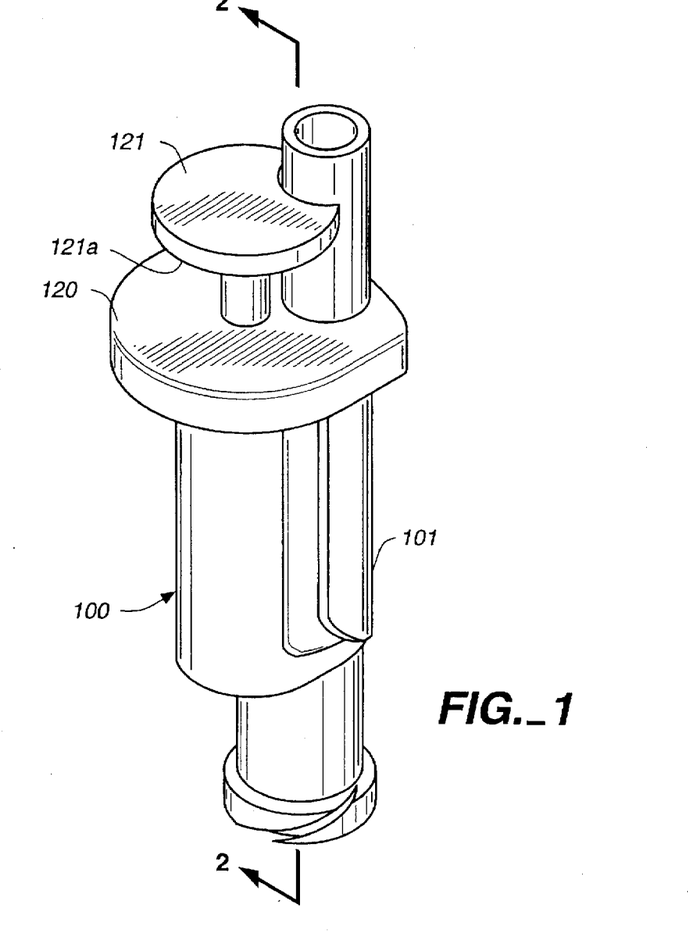
FIG. 1 is a perspective view of the flush device of the present invention.
Figure 2:
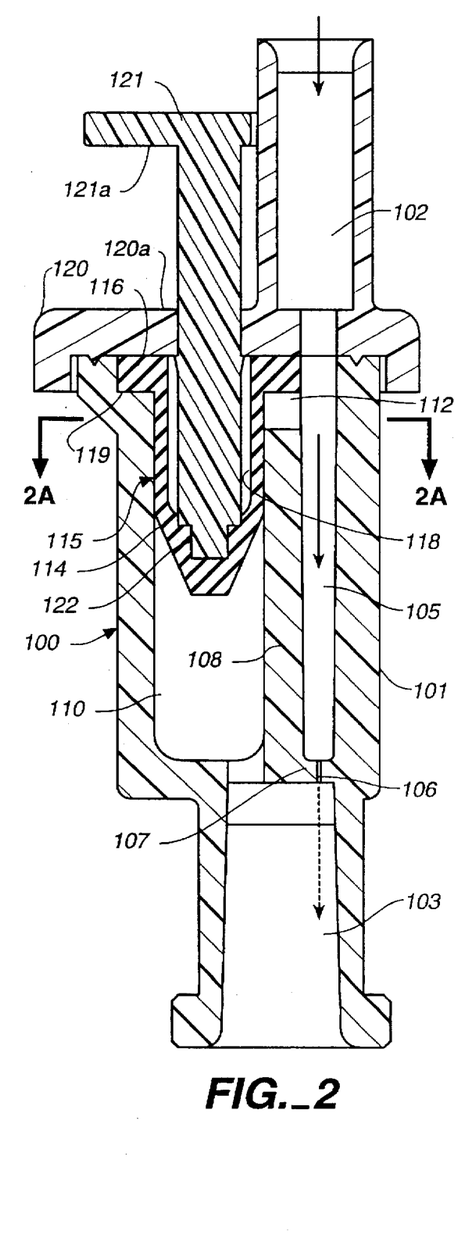
FIG. 2 is a view, partially in section, taken along the lines 2—2 of FIG. 2 of the elastomeric body with the plunger disposed therein in an initial position.
Figure 2A:
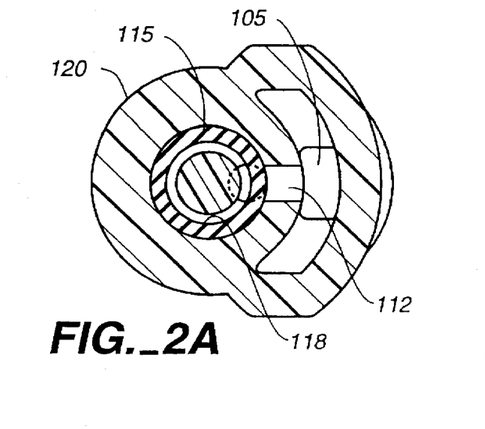
FIG. 2A is a sectional view taken along the lines 2A—2A of FIG. 2.
Figure 3:
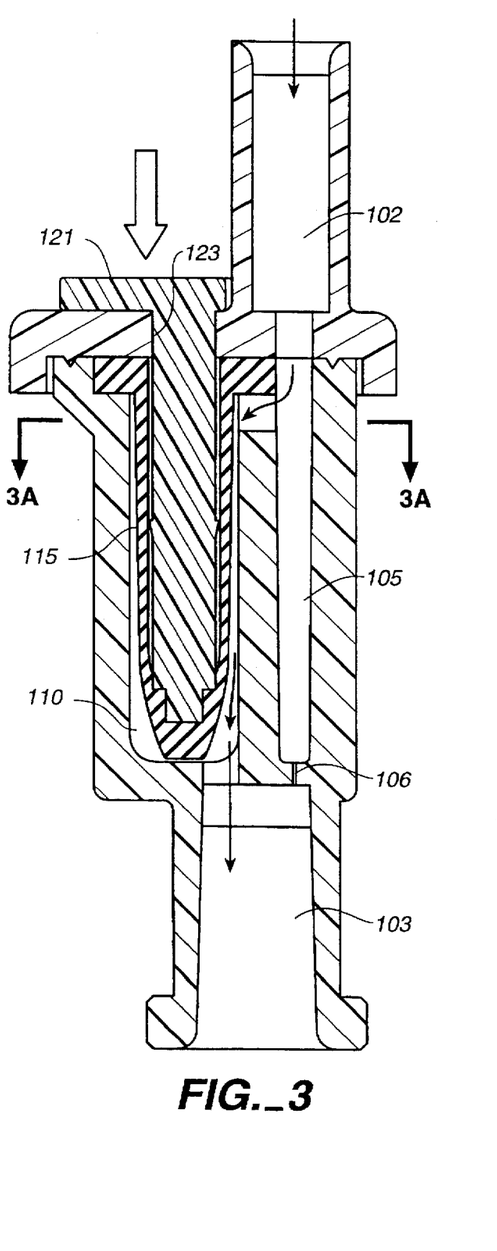
FIG. 3 is a view similar to FIG. 2 wherein the plunger is depressed and the elastomeric body is distended.
Figure 3A:
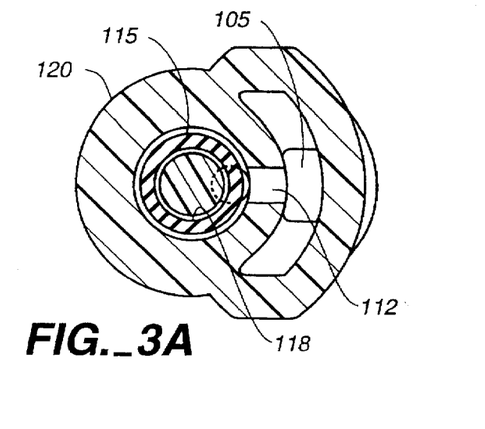
FIG. 3A is a sectional view taken along the lines 3A—3A of FIG. 3.

The flush device of the present invention is best seen in FIGS. 1–3 wherein a device 100 comprises a main body portion 101 having an inlet 102 and an outlet 103. Disposed between the inlet 102 and the outlet 103 are a pair of fluid channels with a fluid channel 105 terminating in a capillary bore 106 which passes from the fluid channel 105 to the fluid outlet 103. The capillary bore 106 enables continuous fluid flow at a low or capillary rate from the inlet 102 to the outlet 103 through the capillary bore 106. The capillary bore 106 is drilled into a bottom wall 107 of the main body portion 101 below the fluid channel 105 as by laser drilling. The use of a laser drilled hole 106 eliminates the need for a glass restrictor or other object inserted in the channel 105 to provide a capillary bore therethrough.

A median wall 108 separates the continuous fluid flow channel 105 from a fast flush channel 110. An opening 112 in the median wall 108 connects the inlet 102 to the fast flush channel 110. An elastomeric member 114 disposed in the fast flush channel 110 blocks the opening 112 in an initial position to prevent fluid from flowing from the inlet 102 through the fast flush channel 110 to the outlet 103.

Elastomeric member 114 comprises a body 115 having an upper annular flange 116 and an internal bore 118. Flange 116 engages an annular shoulder extension 119 of the fast flush channel 110 and a cap 120 captures the annular flange 116 between the annular shoulder and the cap. Plunger 121 extends into the bore 118 of the elastomeric member 115 through an opening 123 in the cap 120 to seat in a shouldered seat 122 provided at the bottom of the interior of the bore of the member 114.

The operation of flush device 100 is as follows. Under a continuous fluid flow condition, there is fluid flow from the input 102 to the output 103 through the capillary bore 3.06 associated with the continuous flow channel 105. The continuous fluid flow rate is at a drip rate and substantially lower than the fluid flow rate when the fast flush channel 110 is open.

To open the fast flush channel 110, elastomeric member 114 is distended by depressing the plunger 121 until the bottom face 121a of the plunger 121 is in close proximity to or engages an upper face 120a of the cap 120 of the flush device 100. When the plunger 121 is depressed, the elastomeric body is distended to the position shown in FIG. 2, to enable fluid flow from the inlet 102 through the opening 112 in the median wall 108 through the fast flush channel 110 and through the outlet 103 at a fast flush rate.

Figures 4, 5:
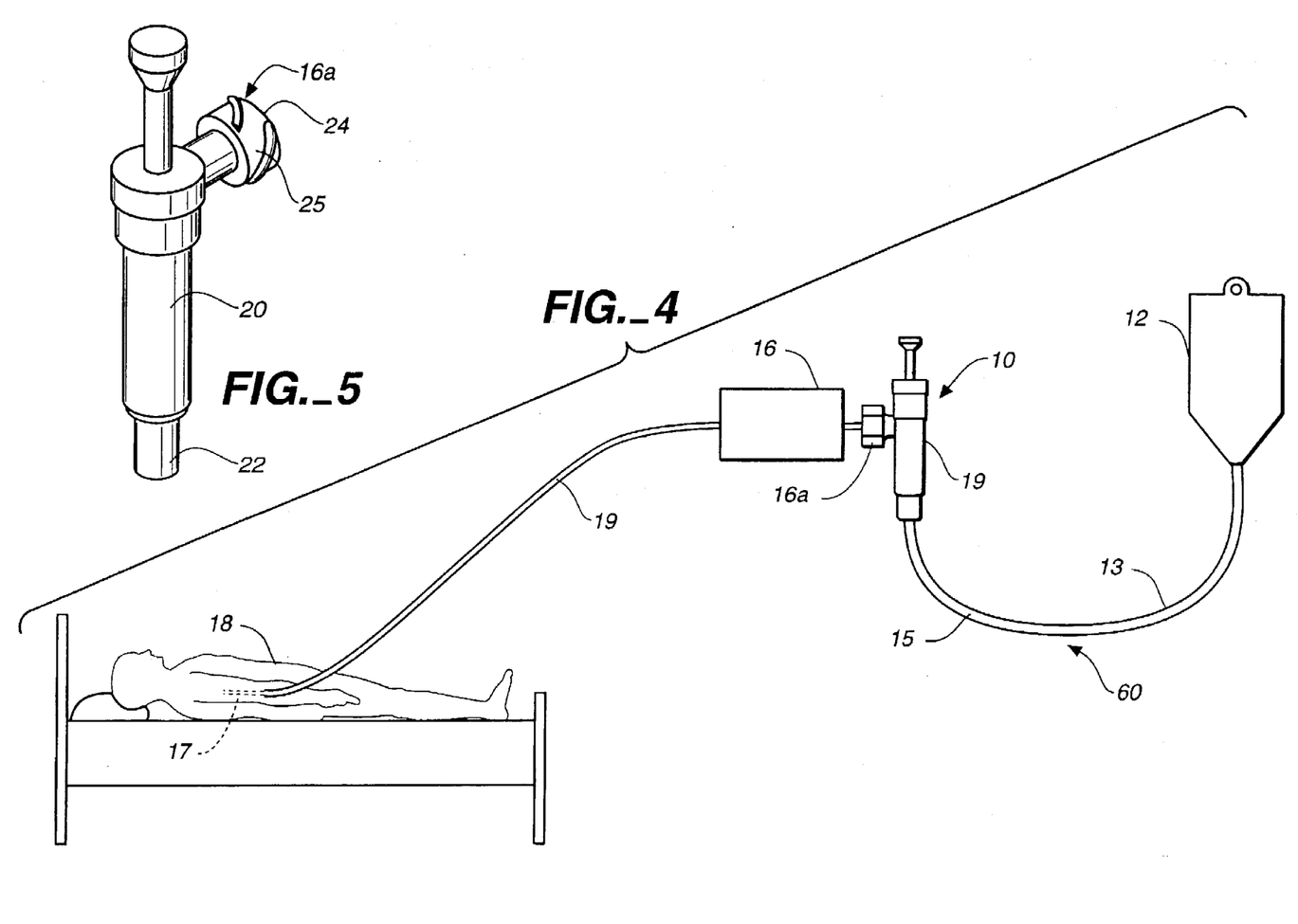
FIG. 4 is a diagrammatic illustration of a system for the intravenous monitoring of the blood pressure in a patient including the device of an alternative embodiment of the present invention.
FIG. 5 is a perspective view of the alternative embodiment of the present invention.
Figure 7:
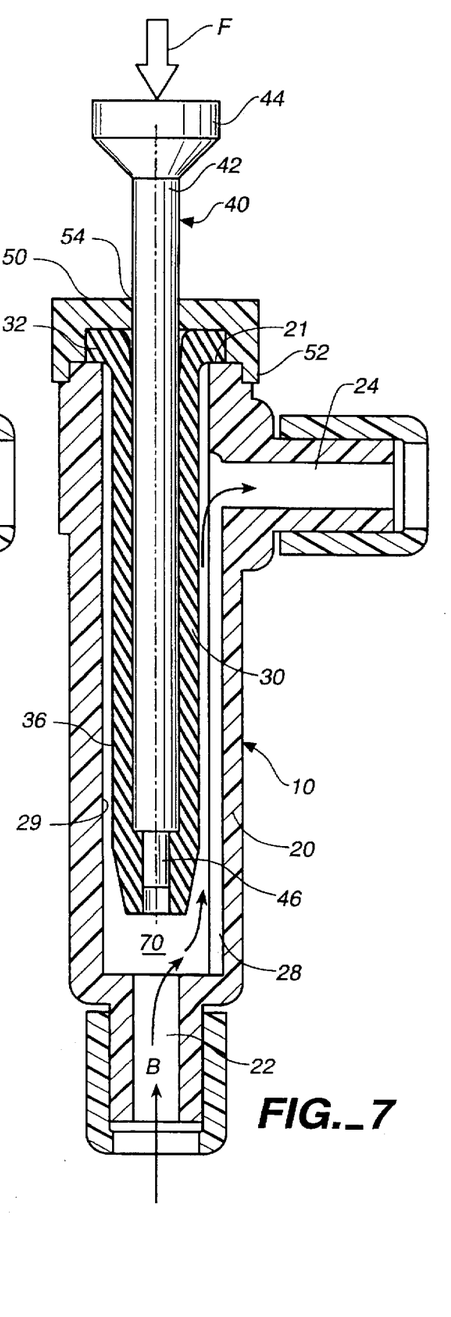
FIG. 7 is a side elevational view partially in section of the alternative embodiment of the present invention in its configuration for providing a fast flush flow.

In FIG. 4, the flush device of an alternative embodiment of the present invention is incorporated into a blood pressure monitoring system 60. The overall system 60 includes a pressurized infusion container 12 connected by a tube 13 to the flush device 10. The flush device 10 is also provided with a fitting 16a to which the transducer 16 is connected. The opposite end of transducer 16 is connected to the catheter 17 by tubing 19. In FIG. 4 the catheter 17 is advanced into the radial artery of a patient 18. The catheter could also be advanced through the jugular vein into the right heart chambers and to the pulmonary artery. The present invention is usable with various catheter systems wherein the catheter may be threaded through the various veins or arteries of the human body. As may be seen best in FIG. 5, the flush device 10 of the alternative embodiment of the present invention includes three essential parts. Specifically, tubular member 20 is formed to contain a similarly shaped elastomeric member 30. Elastomeric member 30 has an internal bore 31 which receives a stem 42 of a plunger 40 which is used to distend the elastomeric member as shown in FIG. 7. The plunger 40 is directly inwardly to distend elastomeric member 30 to move away from the inner wall 29 of tubular member 20.

At the bottom of tubular member 20 is located inlet 22 which may be adapted for connection with various sizes of commonly used medical grade flexible tubing. As shown in FIG. 5, disposed opposite the inlet 22 is an outlet 24. Interposed between the inlet 22 and the outlet 24 is a capillary channel 28 provided in an inner wall of tubular member 20 as by laser drilling. The size of capillary channel 28 is exaggerated in FIGS. 6 and 7 for clarity.

Figure 6:
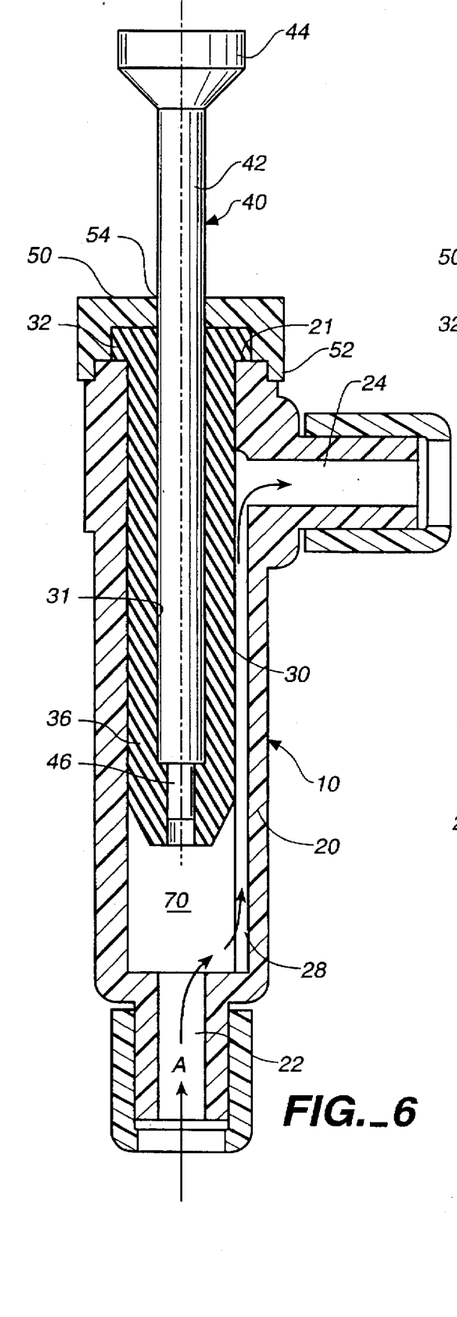
FIG. 6 is a side elevational view partially in section of the alternative embodiment of the present invention in its configuration for providing a continuous or capillary flow.

Retaining elastomeric member 30 within the tubular member 20 is a cap 50. The cap 50 is in frictional engagement with the top 21 of the tubular member 20. The sides 52 of the cap 50 may be sonically welded or sealed to the top 21 of the tubular member 20. The cap 50 further includes an opening 54 which allows for the passage of the stem 42 when the cap 50 is in place on the tubular member 20. A flange 32 at the top of elastomeric member 30 is retained in position by the sealing of the cap 50 at the top 21 of the tubular member 20.

Formed on the top of the plunger 40 is an enlarged head section 44. An end 46 of the plunger 40 is in contact with the bottom 34 of the elastomeric member 30. As shown in FIG. 6, when the elastomeric member 30 is in an initial position, an annular side wall 36 of the elastomeric member 30 will be in sealing engagement with the inner wall 29 of tubular member 20 to provide a closure for the open side of the capillary channel 28.

As shown in FIG. 7, when the elastomeric member 30 is in a distended position, the side wall 36 of the elastomeric member is moved away from sealing engagement with inner wall 29. The movement of the member 30 away from the side of the tubular member 20 allows for increased flow through the tubular member 20 and overflows the capillary channel 28.

As may be best seen in FIG. 5, the outlet 24 further includes adaptations for luer fitments. In the preferred embodiment the outlet port 24 includes a male luer fitment 25.

The alternative embodiment device 10 is utilized in conjunction with an intravenous blood pressure monitoring system 60 as shown in FIG. 4. Such device allows for a continuous low flow of liquid to continually flush the end of catheter 17 indwelling within the body of the patient 18. When desired, however, it may be necessary to fast flush the end of the catheter 17 or provide a square wave for calibration by providing a bolus of fluid from the source of medical fluid 12. This bolus of solution is provided by the flush device of the present invention.

Normal or continuous low flow of fluid is provided by the flush device 10 of the present invention, when elastomeric member 30 is in an initial position as shown in FIG. 6. Therein, as may be seen by arrows labelled A, medical fluid enters the bottom of the device 10 and enters the capillary channel 28 which is formed on the inner wall 29 of the tubular member 20. Fluid then progresses through capillary channel 28 and out through outlet 24 thereby providing a continuous flow of fluid at a capillary or low flow rate to the end of the catheter 17 indwelling within the patient 18.

When it is desired to provide a bolus of solution to the end of the catheter for purging or calibrating with a square wave, force as indicated by arrow F in FIG. 6 is placed upon the enlarged head 44 of the plunger member 40. This force will cause plunger member 40 to move into the interior 70 of tubular member 20 and thus distend elastomeric member 30. The distending of elastomeric member 30 will cause it to move away from inner wall 29 thus breaking sealing engagement with the inner wall. Fluid, as may be seen by arrows B in FIG. 7 will now be allowed to progress through the inlet port 22, the overflow channel around the elastomeric member 30 and then pass out through the outlet 24 without being restricted by the capillary channel 28.

If a sampling device were interposed in line 19 between the patient 18 and the transducer 16, the flush device 10 would also protect the transducer 16 from damage due to overpressurization of the system 60 introduced by improper use of the sampling device; e.g., if the line to the patient were closed and an excessive pressure pulse was delivered to the transducer 16 from the sampling device in error.

The tubular member 20 and the plunger 40 may be formed from any suitable grade medical plastics The elastomeric member 30 may also be formed of a rubber material which is compatible with medical fluids.

Figure 8:
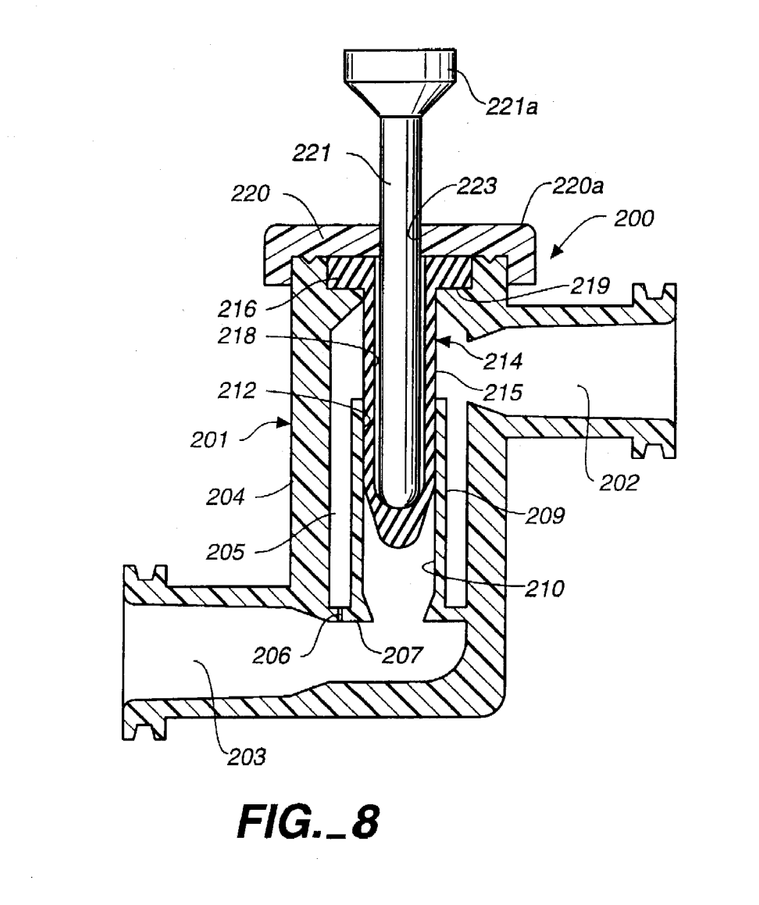
FIG. 8 is a side elevation, shown partially in section, of a second alternative embodiment of the flush device of the present invention.

A second alternative embodiment of the flush device of the present invention is best seen in FIG. 8 wherein a device 200 comprises a main body portion 201 having an inlet 202 and an outlet 203. Disposed between the inlet 202 and the outlet 203 are a pair of fluid channels with an annular fluid channel 205 defined by outer wall 204 and inner wall 209. Fluid channel 205 terminates in a capillary bore 206 which passes from the fluid channel 205 to the fluid outlet 203. The capillary bore 206 enables continuous fluid flow at a low or capillary rate from the inlet 202 to the outlet 203 through the capillary bore 206. The capillary bore 206 is drilled into a bottom wall 207 of the fluid channel 205 as by laser drilling.

The annular wall 209 defines a fast flush channel 210. In an initial position, an elastomeric member 214 disposed in the fast flush channel 210 blocks an upper opening 212 to the flush channel 210 to prevent fluid from flowing from the inlet 202 through the fast flush channel 210 to the outlet 203.

Elastomeric member 214 comprises a body 215 having an upper annular flange 216 and an internal bore 218. Flange 216 engages an annular shoulder extension 219 of the flush device 200 co-extensive with the flush channel 210 and a cap 220 captures the annular flange 216 between the annular shoulder and the cap. Plunger 221 extends into the bore 218 of the elastomeric member 214 through an opening 223 in the cap 220 to engage the bottom of the bore of the member 214.

The operation of flush device 200 is as follows. Under a continuous fluid flow condition, there is fluid flow from the input 202 to the output 203 through the capillary bore 206 associated with the continuous flow channel 205. The continuous fluid flow rate is at a drip rate and substantially lower than the fluid flow rate when the fast flush channel 210 is open.

To open the fast flush channel 210, elastomeric member 214 is distended by depressing the plunger 221 until a head portion 221a of the plunger is in close proximity to or engages an upper face 220a of the cap 220 of the flush device 220. When the plunger 221 is depressed, the body 215 of the elastomeric member 214 is distended, to enable fluid flow from the inlet 202 through the fast flush channel 210 and through the outlet 203 at a fast flush rate.

Figure 9:
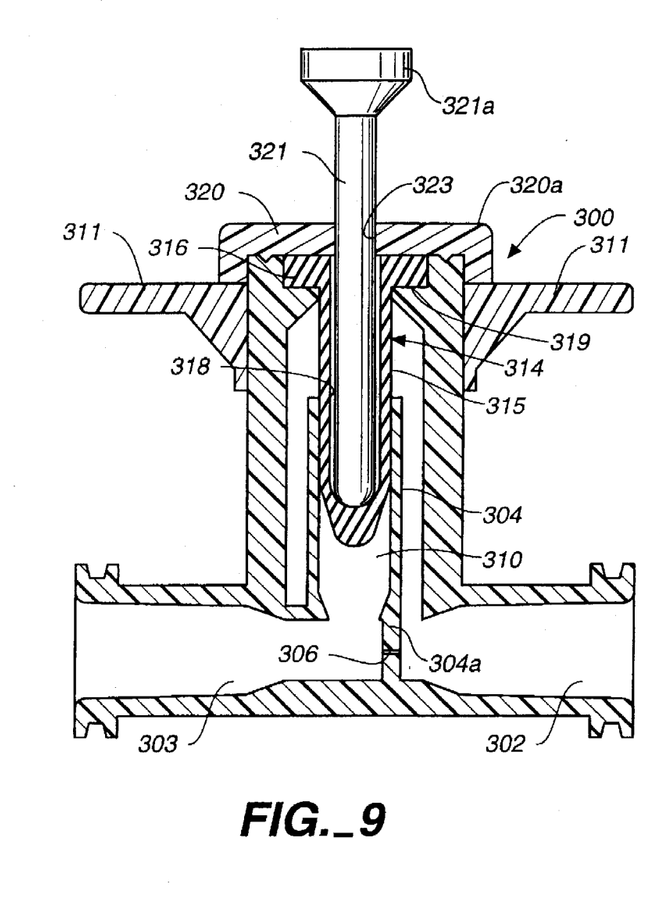
FIG. 9 is a side elevation, shown partially in section, of a third alternative embodiment of the flush device of the present invention.

A third alternative embodiment of the flush device of the present invention is best seen in FIG. 9 wherein a flush device 300 comprises a main body portion 301 having an inlet 302 and an outlet 303. Disposed between the inlet 302 and the outlet 303 is an annular wall 304 having a lower extension 304a disposed between the inlet 302 and the outlet 303. A capillary bore 306 laser drilled through wall 304a enables fluid flow at a capillary rate from the inlet 302 to the outlet 303.

The annular wall 304 defines a fast flush channel 310. Gripping members 311 are disposed on opposite sides of the wall 304. In an initial position, an elastomeric member 314 disposed in the fast flush channel 310 blocks an upper opening 312 to the fast flush channel 310 to prevent fluid from flowing from the inlet 302 through the fast flush channel 310 to the outlet 303.

Elastomeric member 314 comprises a body 315 having an upper annular flange 316 and an internal bore 318. Flange 316 engages an annular shoulder extension 319 of the flush device 300 co-extensive with the flush channel 310 and a cap 320 captures the annular flange 316 between the annular shoulder and the cap. Plunger 321 extends into the bore 318 of the elastomeric member 314 through an opening 323 in the cap 320 to engage the bottom of the bore of the member 314.

The operation of flush device 300 is as follows. Under a continuous fluid flow condition, there is fluid flow from the input 302 to the output 303 through the capillary bore 306 in wall 304a. The continuous fluid flow rate is at a drip rate and substantially lower than the fluid flow rate when the fast flush channel 310 is open.

To open the fast flush channel 310, elastomeric member 314 is distended by engaging gripping members 311 and a head portion 321a of the plunger 321 to depress the plunger 321 until the head portion 321a of the plunger 321 is in close proximity to or engages an upper face 320a of the cap 320 of the flush device 300. When the plunger 321 is depressed, the body 315 of elastomeric member 314 is distended to enable fluid flow from the inlet 302 through the fast flush channel 310 and through the outlet 303 at a fast flush rate.

Figure 10:
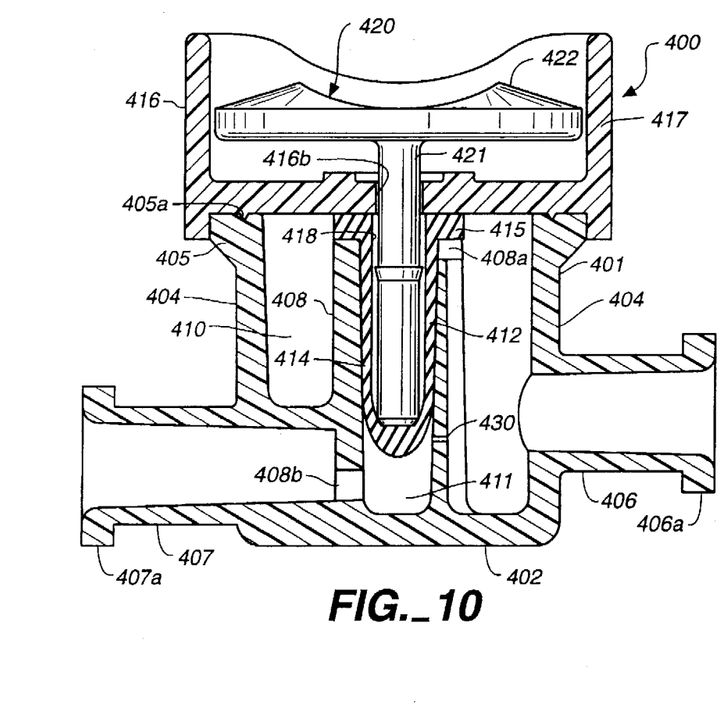
FIG. 10 is a side elevation, shown partially in section of a fourth alternative embodiment of the flush device of the present invention in a mode for providing a continuous or capillary flow.
Figure 11:
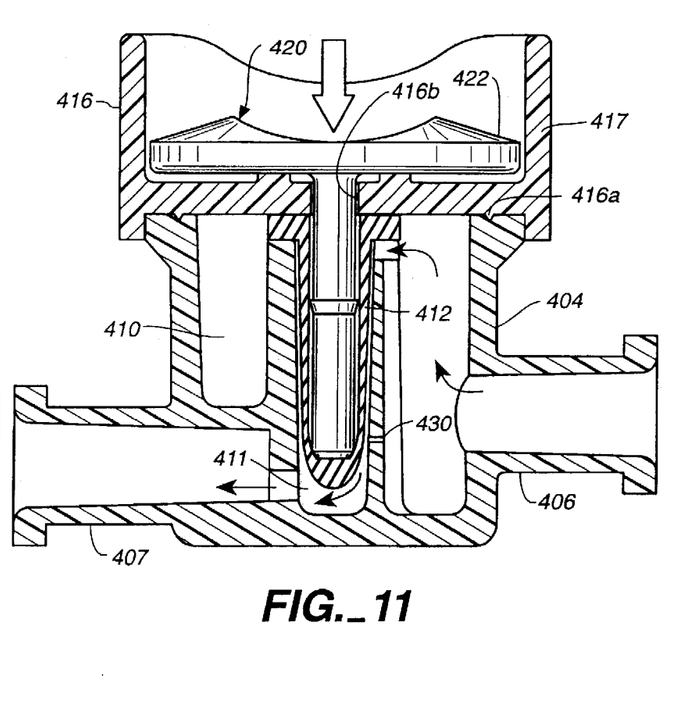
FIG. 11 is a side elevational view partially in section of the fourth alternative embodiment of the flush device of the present invention in a mode for providing a fast flush.

A fourth alternative embodiment is a flush device of the present invention best seen in FIGS. 10 and 11. Flush device 400 comprises a body portion 401 generally oblong in shape and including a base 402 having an annular side wall 404 extending upwardly therefrom. Annular side wall 404 defines the outer perimeter of the body portion 401 and terminates in an annular enlarged portion 405.

Disposed at one side of annular side wall 404 is an inlet tube 406 whose bottom edge is disposed about 0.375 inches above the base 402. Outlet tube 407 is disposed opposite inlet tube 406. The bottom edge of outlet tube 407 is somewhat lower than the bottom edge of inlet tube 406 and slightly above the base 402. Both inlet tube 406 and outlet tube 407 carry at their respective outer ends luer fittings 406a and 407a.

Extending upwardly from the base 402 is a central cylinder 408, whose upper edge is disposed slightly below the upper edge of the widened portion 405 of annular side wall 404. An annular space 410 is defined between the outer face of cylinder 408 and outer side wall 404. The cylinder 408 includes an upper opening 408a adjacent the inlet side of the flow device 400 and a opening 408b adjacent the outlet side of the device 400 at the bottom thereof adjacent the base 402.

A bore 411 is defined by the cylinder 408. Disposed within the bore 411 is an elastomeric member 412 having an elongated body portion 414 and an upper annular shoulder 415. Body portion 414 of the elastomeric member 412 extends into the bore 411 with a shoulder 415 resting at an upper edge of cylinder 408. The upper face of shoulder 415 is generally aligned with the upper face of the enlarged portion 405 of outer wall 404.

A cap or cover 416 overlies body portion 401, engaging body portion 401 at enlarged portion 405 of outer annular wall 404 with an annular projection 416a in cover 416 engaging an annular notch 405a of enlarged portion 405, enabling the cover to be secured in place on the enlarged portion 405 as by sonic welding.

The cover 416 traps shoulder 415 of elastomeric member 412 between an upper edge of cylinder 408 and the cover 416. The cover 416 also includes an upwardly extending outer wall 417. A bore 418 of elastomeric member 412 receives a cylindrical body portion or stem 421 of a plunger 420. Body portion 421 is inserted into bore 418 through an aligned complementary opening 416b in the cover 416.

A plunger end cap 422 engages the distal end of the plunger 420 and is enclosed within outer wall 417 of the cover 416 of the device 400.

To understand the operation of the fluid flow device 400 of FIGS. 10 and 11 it is necessary to consider FIGS. 10 and 11 separately. Fluid flow from inlet 406 fills the annular channel 410 between outer annular wall and cylinder 408. Elastomeric member 412 in the position shown in FIG. 10 blocks flush fluid flow through opening 408a at the inlet side of cylinder 408. Thus continuous capillary flow passes from the inlet 406 through a laser drilled hole 430 in the inlet side of cylinder 408.

To initiate fast flush plunger 420 is depressed, extending elastomeric member 412 to open fluid passage 408a so that fluid is introduced through fluid opening 408a at a fast flush rate to flow down the bore 411 to exit the device 400 at outlet opening 408b through outlet 407. Filling channel 410 with fluid minimizes turbulent flow when fast flush is initiated, as well as minimizing air gaps during capillary flow.

There is now provided by the present invention a flush device which will allow continuous low flow of fluid from a fluid source to an indwelling blood pressure monitoring catheter, allow for a continuous flow of medical fluid through the catheter when desired and provide pressure relief to protect the transducer in a blood pressure monitoring system.

Although the flush device of the present invention has been described with respect to its preferred embodiment hereof, it is, however, not intended that the present fast flush device be limited to such embodiment only, but rather it should be defined by the scope of the appended claims.

We claim:

1. A flush device for use in fluid flow systems employed for administering, a medicinal fluid to a patient, comprising:
   (a) a housing having a tubular body including an inner cylinder and an outer annular wall and including an inlet and an outlet;
   (b) an interior fluid entry chamber disposed between said inner cylinder and said outer annular wall, said interior fluid entry chamber being in fluid communication with the inlet for receiving the medical fluid, said outlet being adapted for coupling to a catheter through which the medical fluid flows to the patient;
   (c) a capillary bore comprising part of a non-closable first fluid flow path from said inlet to said outlet that extends through said fluid entry chamber and said inner cylinder, said capillary bore being disposed in a wall of said inner cylinder and extending through said wall between the fluid entry chamber and an interior of said inner cylinder, connecting said fluid entry chamber in fluid communication with said outlet to provide a slow flow of medicinal fluid through the flush device along the first fluid flow path;
   (d) a closable second fluid flow path extending through the interior of said inner cylinder from said inlet to said outlet and coupling said interior fluid entry chamber in fluid communication with said outlet, said second fluid flow path providing a substantially greater rate of flow of the medicinal fluid through the housing, said flush device further comprising a member disposed within the interior of said inner cylinder, said member comprising an elastically deformable material and having a portion positioned to press against the wall of said inner cylinder to close off said second flow path, said first and second fluid flow paths being substantially in parallel; and
   (e) a plunger movably coupled to said housing and positioned to distend said member within said inner cylinder, thereby reducing a cross-sectional area of said member and causing said member to move away from the wall of said inner cylinder to open said second fluid path between the inlet and the outlet.

2. The flush device of claim 1, wherein the inlet is coupled to the interior fluid entry chamber through an inlet tube, and an outlet tube couples the inner cylinder to the outlet, said outlet tube being disposed generally opposite the inlet tube.

3. The flush device of claim 1, wherein the housing includes a base that comprises an inlet tube extending between the inlet and the interior fluid entry chamber, and an outlet tube that extends between the inner cylinder and the outlet, said inlet tube and said outlet tube being disposed on opposite sides of the housing and generally in parallel alignment with each other.

4. The flush device of claim 1, wherein the housing further comprises a base, a main body portion mounted on the base in which the inner cylinder and the interior fluid entry chamber are disposed, and a cap sealingly mounted on the main body portion, overlying said inner cylinder.

5. The flush device of claim 4, wherein said member comprises an elongated body portion, and wherein an annular shoulder is provided at an upper end of said body portion, said body portion being received into the inner cylinder, the annular shoulder engaging an upper edge of the inner cylinder, and said cap being mounted on the main body portion of the housing to trap said shoulder between the upper edge of the inner cylinder and the cap.

6. The flush device of claim 4, wherein the cap includes a generally annular wall extending around a periphery of the cap, said plunger including an elongated portion and a push button mounted on an outwardly extending end of said elongated portion and surrounded by the annular wall of the cap, the elongated portion of the plunger being received in an opening in the cap in which it is reciprocatively movable and extending into a bore provided in said member, whereby inward movement of the plunger distends the member disposed in the inner cylinder drawing the member away from the wall of the inner cylinder to open said second fluid path, thereby enabling a fast flushing flow of medicinal fluid through the device alone the second fluid path.

7. A flush device for selectively providing alternative flow rates of a medicinal fluid through the device, including a fast flushing flow rate and a substantially slower flow rate, comprising:
   (a) a housing in which are formed an inner chamber and an adjacent entry chamber separated from the inner chamber by a wall, said housing including an inlet port coupled in fluid communication to the entry chamber and an outlet port coupled in fluid communication with the inner chamber;
   (b) a capillary bore disposed in the wall separating the inner chamber from the entry chamber, connecting the entry chamber in fluid communication with the inner chamber;
   (c) a first fluid path through the flush device providing the relatively slower flow rate and coupling the inlet port to the outlet port, said first fluid path including:
      (i) the entry chamber;
      (ii) the capillary bore; and
      (iii) the inner chamber;
   (d) an opening through the wall separating the entry chamber from the inner chamber, said opening being substantially larger in a cross-sectional size than the capillary bore;
   (e) an elastomeric member disposed in the inner chamber in sealing contact with the wall separating the entry chamber from the inner chamber; and
   (f) a plunger seated in the elastomeric member and extending from the housing, said plunger, when selectively depressed into the housing, elongating the elastomeric member and forcing the elastomeric member away from contact with the wall separating the entry chamber from the inner chamber to produce a second flow path through the device coupling the inlet in fluid communication with the outlet, said second flow path providing the fast flushing flow rate and including:
      (i) the entry chamber;
      (ii) the opening in the wall separating the entry chamber from the inner chamber; and
      (iii) the inner chamber, said second fluid path being generally parallel to said first fluid path.

8. The flush device of claim 7, wherein the entry chamber is generally annular and extends around the inner chamber.

9. The flush device of claim 7, wherein the housing includes an inlet tube coupling the inlet port to the entry chamber, and an outlet tube coupling the inner chamber to the outlet port.

10. The flush device of claim 9, wherein the housing is generally cylindrical in shape, and wherein the inlet tube and the outlet robe extend outwardly from different positions on an outer cylindrical surface of the housing.

11. The flush device of claim 9, wherein the housing further includes a main body portion in which the entry chamber and the inner chamber are disposed, and a cap that sealingly covers the inner chamber.

12. The flush device of claim 11, wherein the plunger includes an elongate portion that extends through an opening in the cap to engage the elastomeric member and a push button attached to an outward extending end of the elongate portion of the plunger, said button providing a surface on which a force is applied to extend the elastomeric member, forcing the elastomeric member away from the opening through the wall separating the inner chamber and the entry chamber, to enable the fast flushing flow rate.

13. The flush device of claim 7, wherein the inner chamber is generally cylindrical in shape and said wall separating the entry chamber from the inner chamber defines an inner cylindrical surface of the inner chamber.

* * * * *